(12) United States Patent
Ikeda (10) Patent No.: US 10,694,926 B2
(45) Date of Patent: Jun. 30, 2020

(54) FLEXIBLE TUBE INSERTION APPARATUS HAVING VIBRATION ACTUATOR FOR REDUCING INSERTION FORCE OF ENDOSCOPE INSERTION MEMBER

(71) Applicant: OLYMPUS CORPORATION, Tokyo (JP)

(72) Inventor: Yuichi Ikeda, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 361 days.

(21) Appl. No.: 15/823,707

(22) Filed: Nov. 28, 2017

(65) Prior Publication Data

US 2018/0078122 A1 Mar. 22, 2018

Related U.S. Application Data

(63) Continuation of application No. PCT/JP2015/065367, filed on May 28, 2015.

(51) Int. Cl.
*A61B 1/00* (2006.01)
*A61B 1/005* (2006.01)
(Continued)

(52) U.S. Cl.
CPC ...... *A61B 1/00133* (2013.01); *A61B 1/00006* (2013.01); *A61B 1/0016* (2013.01);
(Continued)

(58) Field of Classification Search
CPC ............ A61B 1/00133; A61B 1/00006; A61B 1/0051; A61B 1/00096; A61B 1/00156;
(Continued)

(56) References Cited

U.S. PATENT DOCUMENTS 5,060,632 A * 10/1991 Hibino ............... A61B 1/00039
348/65
5,159,446 A * 10/1992 Hibino ............... A61B 1/00039
348/65
(Continued)

FOREIGN PATENT DOCUMENTS

JP 2002233497 A 8/2002
JP 2002282204 A 10/2002
(Continued)

OTHER PUBLICATIONS

English translation of International Preliminary Report on Patentability dated Dec. 7, 2017 together with the Written Opinion received in related International Application No. PCT/JP2015/065367.
(Continued)

*Primary Examiner* — John P Leubecker
(74) *Attorney, Agent, or Firm* — Scully, Scott, Murphy & Presser, P.C.

(57) ABSTRACT

A flexible tube insertion apparatus includes an insertion section inserted into a tube and a detection unit that detects states of the insertion section. The flexible tube insertion apparatus includes one or more vibrators that are arranged in the insertion section, generate vibration, and vibrate the insertion section by the generated vibration and a controller that calculates a magnitude of an external force applied to the insertion section from the tube based on the states of the insertion section detected by the detection unit, computes a resonance frequency of the vibration relative to the magnitude of the external force, and controls the vibrators in such a manner that the vibrators vibrate at the resonance frequency.

14 Claims, 8 Drawing Sheets

(51) Int. Cl.
*A61B 34/20* (2016.01)
*A61B 1/06* (2006.01)

(52) U.S. Cl.
CPC ........ *A61B 1/0055* (2013.01); *A61B 1/00096* (2013.01); *A61B 1/0676* (2013.01); *A61B 2034/2061* (2016.02)

(58) Field of Classification Search
CPC . A61B 1/0016; A61B 1/01; A61B 2034/2061; A61B 2562/0247; A61B 2562/0261
See application file for complete search history.

(56) References Cited

U.S. PATENT DOCUMENTS

| | | | | |
|---|---|---|---|---|
| 2007/0244354 A1* | 10/2007 | Bayer | ................ | A61B 1/00147 600/106 |
| 2010/0152536 A1* | 6/2010 | Iwasaki | ............. | A61B 1/00154 600/114 |
| 2012/0109184 A1* | 5/2012 | Spivey | ............. | A61B 17/00234 606/205 |
| 2012/0209303 A1* | 8/2012 | Frankhouser | ........ | A61B 10/025 606/169 |
| 2014/0276923 A1* | 9/2014 | Miller | ................ | A61B 17/2202 606/128 |
| 2014/0378760 A1* | 12/2014 | Ito | .......................... | A61B 5/065 600/103 |
| 2015/0057575 A1 | 2/2015 | Tsusaka et al. | | |

FOREIGN PATENT DOCUMENTS

| | | |
|---|---|---|
| JP | 2010142372 A | 7/2010 |
| WO | 2014010177 A1 | 1/2014 |

OTHER PUBLICATIONS

International Search Report dated Aug. 25, 2015 issued in PCT/JP2015/065367.

* cited by examiner

FLEXIBLE TUBE INSERTION APPARATUS HAVING VIBRATION ACTUATOR FOR REDUCING INSERTION FORCE OF ENDOSCOPE INSERTION MEMBER

CROSS-REFERENCE TO RELATED APPLICATIONS

This application is a Continuation Application of PCT Application No. PCT/JP2015/065367, filed May 28, 2015, the entire contents of all of which are incorporated herein by references.

BACKGROUND OF THE INVENTION

1. Field of the Invention

The present invention relates to a flexible tube insertion apparatus.

2. Description of the Related Art

An endoscope disclosed in Jpn. Pat. Appln. KOKAI Publication No. 2002-233497, for example, includes an insertion section inserted into a lumen, and the insertion section includes a rotation member and a motor that drives the rotation member. The rotation member and the motor are arranged inside a distal end portion of the insertion section. The center of gravity of the rotation member is deviated from the center of the rotation member. Accordingly, when the rotation member is rotated by the motor, the rotation causes vibration. This vibration prevents adhesion of the insertion section to the internal wall of the lumen, and reduces friction of the inner wall against the insertion section that contacts the internal wall. This improves the ease of insertion of the insertion section.

BRIEF SUMMARY OF THE INVENTION

One embodiment of the present invention is a flexible tube insertion apparatus comprising an insertion section inserted into a tube, a detection unit that detects states of the insertion section, one or more vibrators that are arranged in the insertion section, generate vibration, and vibrate the insertion section by the generated vibration; and a controller that calculates a magnitude of an external force applied to the insertion section from the tube based on the states of the insertion section detected by the detection unit, computes a resonance frequency of the vibration relative to the magnitude of the external force, and controls the vibrators in such a manner that the vibrators vibrate at the resonance frequency.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

An embodiment of the present invention will be explained in detail with reference to the accompanying drawings. For the sake of clarification, some of the members are not shown in some of the drawings.

First Embodiment

The first embodiment will be described with reference to FIGS. 1, 2, 3A, 3B, 4A, 4B, and 4C.

Figure 1:
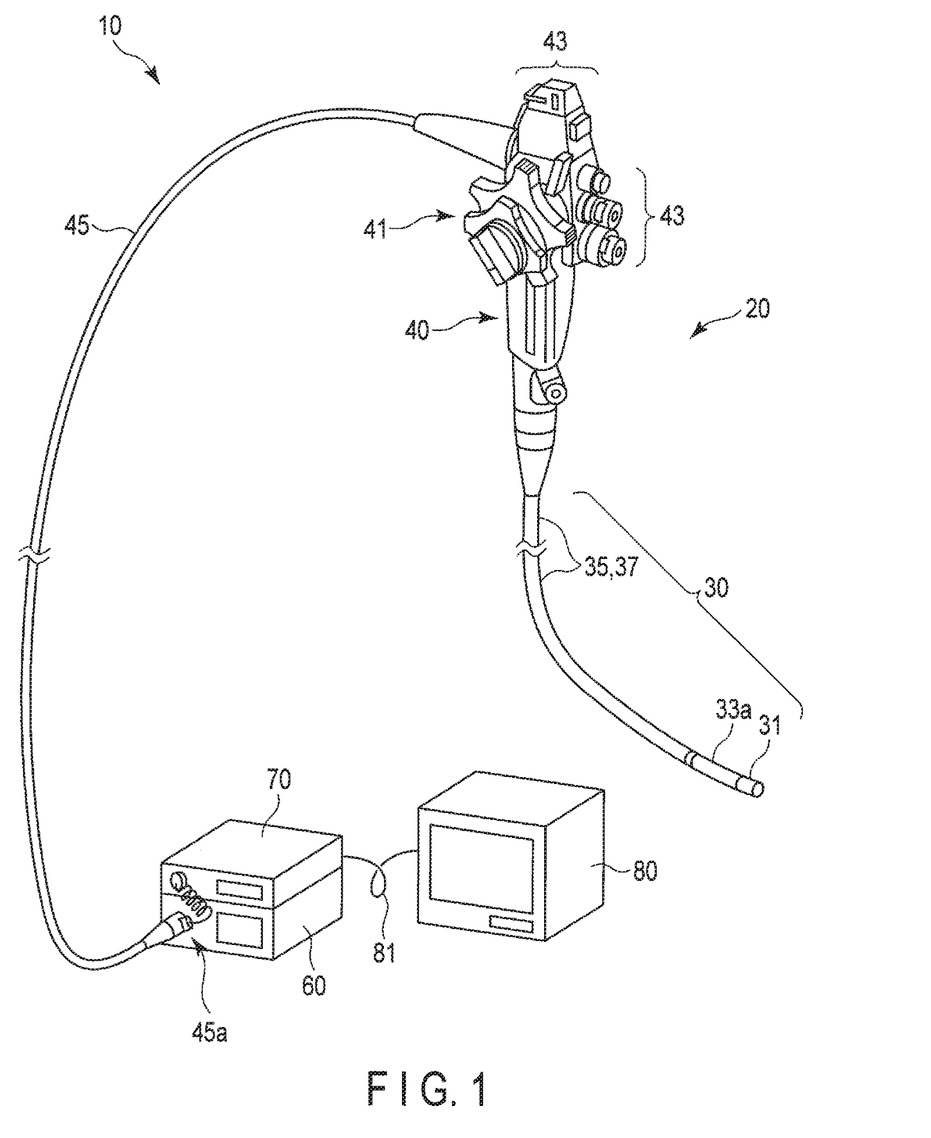
FIG. 1 is a schematic diagram showing a flexible tube insertion apparatus according to a first embodiment of the present invention.

A flexible tube insertion apparatus (hereinafter referred to as an insertion apparatus 10), which is an endoscope apparatus as shown in FIG. 1, is provided in, for example, an operating room or an examination room. The insertion apparatus 10 comprises an endoscope 20, a light source device 60, a control device 70, and a display device 80.

The endoscope 20 functions as, for example, an insertion device inserted into a tube 200 (see FIG. 4A), such as the large intestine. The endoscope 20 images the inside of the tube 200 using an imager (e.g., a CCD or a CMOS) of an image pickup unit (not shown).

The light source device 60 emits light for the imager to perform the imaging. The light is guided by a light guide (e.g., an optical fiber) of an illumination unit (not shown) provided inside the endoscope 20 to an illumination section (not shown, e.g., a phosphor) of the illumination unit. The light is emitted from the illumination section toward the outside as illumination light. The light source device 60 is connected to the control device 70 via a connector 45a. An image taken by the imager is output to the control device 70 from the imager via a signal line of the image pickup unit provided inside the endoscope 20.

The control device 70 processes the image taken by the imager. The control device 70 controls the endoscope 20, the light source device 60, and the display device 80. As will be described later, the control device 70 controls a vibrator (vibration portion) 100 arranged in an insertion section 30 of the endoscope 20.

The display device 80 displays the image taken by the imager and processed by the control device 70. The display device 80 is connected to the control device 70 via the cable 81.

The endoscope 20 is used as an illustration of, for example, the insertion device. The insertion device may be a medical endoscope 20 inserted into a tube 200, such as the large intestine or tract, as in the present embodiment, but is not limited thereto. The insertion device may be an industrial endoscope 20 inserted into a tube 200 of an industrial product such as a pipe, or an insertion tool such as a catheter that includes an illumination optical system. If the insertion device is an industrial endoscope 20, the tube 200 is, for example, conduit. The endoscope 20 may be a front-viewing endoscope 20, or a side-viewing endoscope 20.

Figure 2:
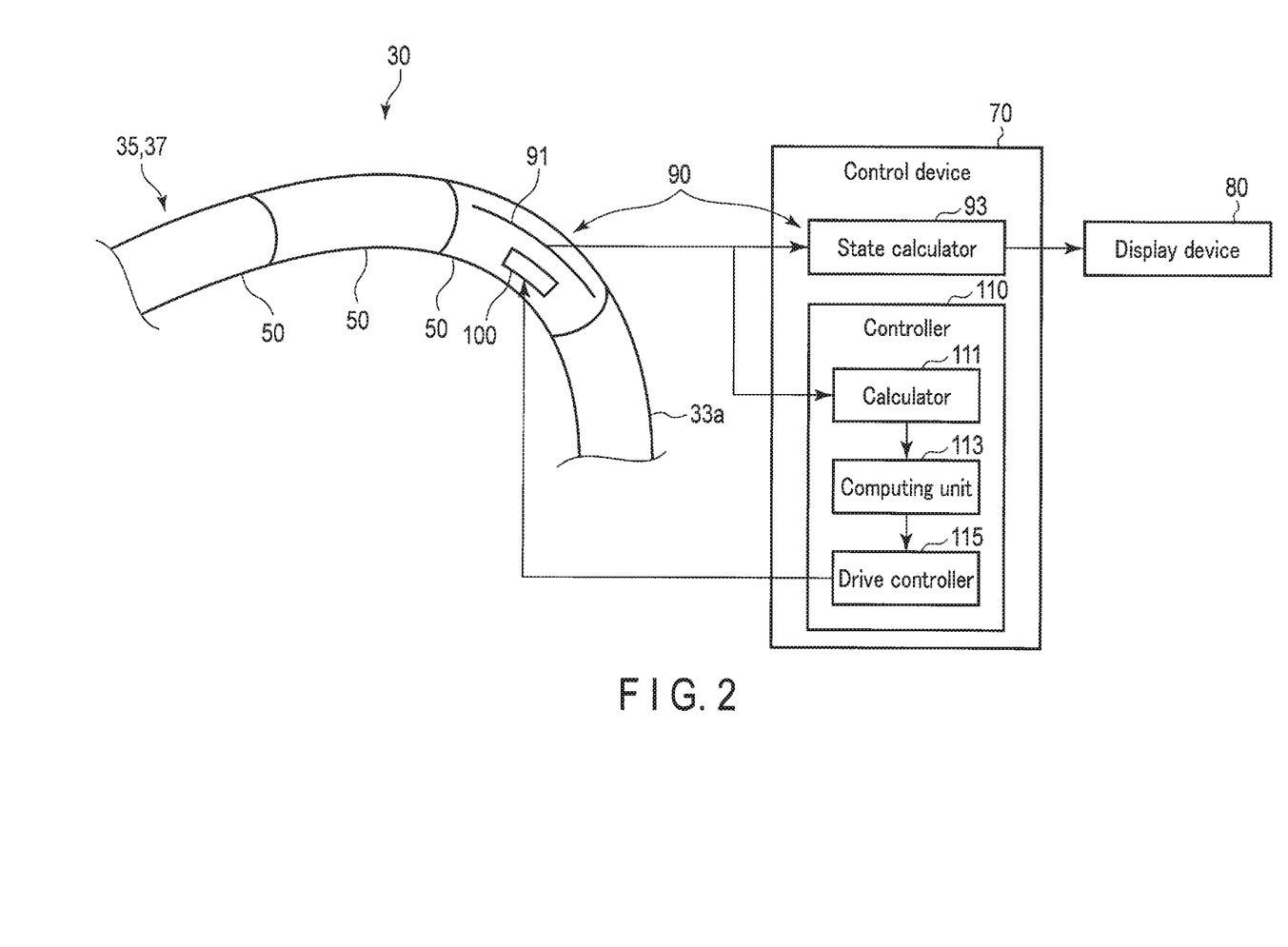
FIG. 2 is a diagram illustrating a relationship between segments, a detection unit, a controller, and a vibrator.

As shown in FIG. 1, the endoscope 20 includes the insertion section 30 inserted into a tube 200 and an operation section 40 coupled to a proximal end portion of the insertion section 30. As shown in FIG. 2, the insertion section 30 is partitioned into a plurality of segments 50 arranged in a row along the axial direction of the insertion section 30. The segments 50 may function as unreal, imaginary regions, or function as real structures.

The insertion section 30 is tubular, elongated, and flexible. The insertion section 30 includes, from a distal end portion of the insertion section 30 to the proximal end portion of the insertion section 30, a distal rigid portion 31, an active bendable portion 33a, and a flexible tube (flexible tube portion) 35. A proximal end portion of the distal rigid portion 31 is coupled to a distal end portion of the active bendable portion 33a, a proximal end portion of the active bendable portion 33a is coupled to a distal end portion of the flexible tube 35, and a proximal end portion of the flexible tube 35 is coupled to the operation section 40. The imager and the illumination section are provided inside the distal rigid portion 31. The active bendable portion 33a actively bends in response to an operation of the operation section 40 coupled to the insertion section 30. Upon receipt of an external force F2 (see FIG. 4A), the active bendable portion 33a may be passively bent by the external force F2. The active bendable portion 33a, which is bent by the external force F2, is bendable to follow the shape inside of the tube 200.

The flexible tube 35 is flexible and is passively bent by the external force F2. Thus, the flexible tube 35 bent by an external force is bendable to follow the shape of the tube 200. The flexible tube 35 has a length greater than that of the active bendable portion 33a. The distal end portion of the flexible tube 35 may include the active bendable portion 33a.

The operation section 40 includes the bendable operation portion 41, which operates the active bendable portion 33a, and a switch 43, which operates each unit including an image pickup unit and an illumination unit. The operation section 40 further includes a universal cord 45, and is connected to the light source device 60 and the control device 70 via the connector 45a of the universal cord 45.

As shown in FIG. 2, the insertion apparatus 10 comprises a detection unit 90 that detects the states of the insertion section 30. The detection unit 90 starts detection when an operation section (not shown) is operated, and constantly performs detection. The timing of the detection may be at every predetermined period of time, and is not limited to a particular timing.

As shown in FIG. 2, the detection unit 90 includes a state detector (state detection portion) 91 that is arranged inside the insertion section 30, and a state calculator (state calculation portion) 93 that is arranged in the control device 70 and calculates the states of the insertion section 30 on the basis of the result of the detection of the state detector 91.

Preferably, the state detector 91 is arranged in combination with the vibrator 100, which will be described later. In this case, it is particularly preferable that the state detector 91 should be arranged in a segment 50 that is at the distal end portion of the flexible tube 35 and close to the active bendable portion 33a.

Although not shown, the state detector 91 may be arranged in at least each of the segments 50. For example, one state detector 91 may be arranged in one segment 50. Thus, each state detector 91 is apart from another state detector 91 along the axial direction of the insertion section 30.

The state detector 91 detects the states of the insertion section 30, such as a bending radius of the insertion section 30, a bending strain of the insertion section 30 distorted by the load externally applied to the insertion section 30, and a pressure that is the load applied to the insertion section 30. The state detector 91 of the detection unit 90 may detect at least one of the bending radius of the insertion section 30, the bending strain of the insertion section 30, and the pressure applied to the insertion section 30, which are included in the states of the insertion section 30. The state detector 91 includes, for example, at least one of a coil that generates a magnetic field in response to the states of the insertion section 30, an output section that outputs electromagnetic waves, ultrasound waves, or the like in response to the states of the insertion section 30, an optical fiber sensor that is variable in progress ratio of light in response to the states of the insertion section 30, a strain sensor, and an absorption member that absorbs X rays in response to the states of the insertion section 30.

The state detector 91 is connected, for example, to the state calculator 93 by wire or wirelessly, and outputs a result of the detection by the state detector 91 to the state calculator 93.

The state calculator 93 is connected to the display device 80. The display device 80 displays the current states of the insertion section 30 in the tube 200 on the basis of the result of the calculation by the state calculator 93. The display is provided in, for example, a three-dimensional manner. On the basis of the states of the insertion section 30 displayed on the display device 80, the operator is capable of monitoring the position and states of the insertion section 30 in the tube 200.

As shown in FIG. 2, the insertion apparatus 10 includes one or more vibrators 100 that is incorporated into the insertion section 30, and generate vibration. The vibrator 100 vibrate the insertion section 30 by the generated vibration. The vibrator 100 vibrates the insertion section 30 to reduce the frictional force between the tube 200 and the insertion section 30.

The vibrator 100 is arranged around, for example, the active bendable portion 33a. Specifically, the insertion section 30 includes the interposed section 37 interposed between the active bending portion 33a and the operation section 40, and the interposed section 37 includes a distal end portion coupled to the proximal end portion of the active bending portion 33a. In the present embodiment, one vibrator 100 is arranged, and the vibrator 100 is arranged at a distal end portion of the interposed section 37. In the present embodiment, the interposed section 37 functions as the flexible tube 35. In the present embodiment, the vibrator 100 should preferably be arranged in a segment 50 that is at the distal end portion of the flexible tube 35 and close to the active bendable portion 33a. Furthermore, the at least one state detector 91 should preferably be arranged in the segment 50 that includes the vibrator 100 and forms one unit together with the vibrator 100.

The vibrator 100 includes, for example, a driving section, which is a motor, and a weight member that is attached to an axial portion of the driving section in an eccentric state and rotates by a driving force of the driving section. The vibrator 100 is, for example, a vibration motor. When the driving section drives and rotates the weight member, the vibrator 100 generates vibration due to the eccentricity of the weight member.

The vibrator 100 may include a voice coil motor. The voice coil motor includes a pair of permanent magnets, and an electromagnet, which is a coil interposed between the permanent magnets, arranged in a magnetic field of the permanent magnets, and driven when an electric current flows therethrough. When the electromagnet is driven, the vibrator 100 generates vibration.

The vibrator 100 may function as a vibrating body that includes a piezoelectric element. The piezoelectric element generates vibration when a voltage is applied.

As shown in FIG. 2, the insertion apparatus 10 comprises a controller (control section) 110 that controls vibration generated by the vibrator 100 on the basis of the states of the insertion section 30 detected by the detection unit 90. The controller 110 is arranged in the control device 70. The controller 110 and the state calculator 93 are configured of a hardware circuit including, for example, an ASIC. At least one of the controller 110 and the state calculator 93 may be configured by a processor, including, for example, a CPU. When at least one of them is configured by a processor, an internal or external memory (not shown) that can be accessed by the processor is provided. The internal or external memory stores a program code that causes the processor to function as at least one of the controller 110 and the state calculator 93 when the processor executes the program code. The controller 110 and the state calculator 93 may be configured using one processor, or may be configured using a plurality of processors. In the latter case, data may be transmitted to and received from each other in such a manner that processing is performed in cooperation. Furthermore, in the latter case, the processors may be arranged in different housings.

The controller 110 includes a calculator (calculate unit) 111 that calculates the magnitude of the external force F2 applied to the insertion section 30 from the tube 200 on the basis of the states of the insertion section 30, which is the result of the detection by the state detector 91. The states of the insertion section 30 indicate, for example, one of the bending radius, the bending strain, and the pressure. The magnitude of the external force F2 is an external force in a position detected by the state detector 91. In general, the bending stiffness of the insertion section 30 is known as a design value. Accordingly, the calculator 111 calculates the external force F2 using Hooke's law on the basis of the bending stiffness and the states of the insertion section 30.

Figure 3A:
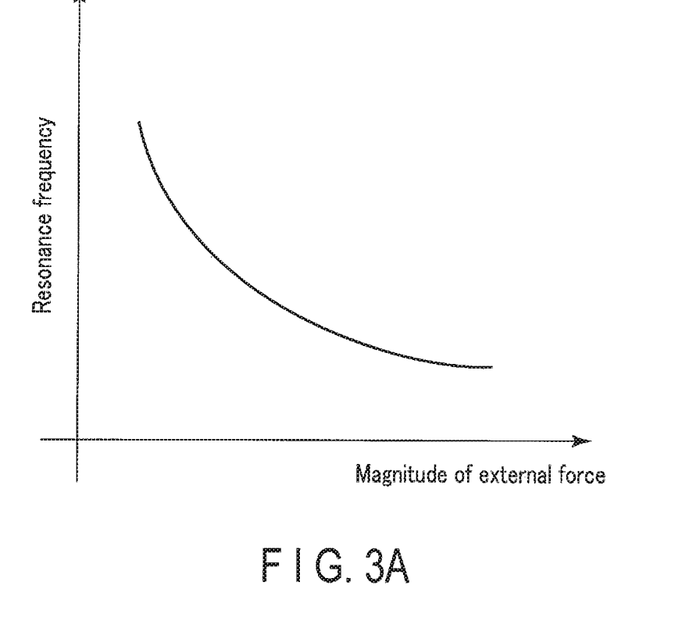
FIG. 3A is a diagram illustrating a relationship between the magnitude of an external force and the resonance frequency.
Figure 3B:
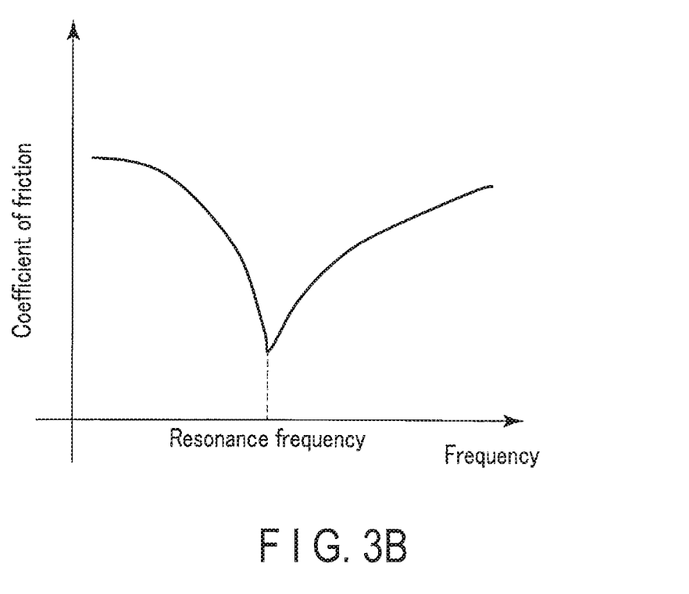
FIG. 3B is a diagram illustrating a relationship between the frequency including the resonance frequency and the coefficient of friction.

As shown in FIG. 3A, the resonance frequency of an object generally changes according to the magnitude of the external force F2 applied to the object, in such a manner that the resonance frequency decreases as the magnitude of the external force F2 increases. As shown in FIG. 3B, when an object vibrates, the coefficient of friction is generally the lowest at the resonance frequency of all the frequencies. Accordingly, the controller 110 includes the computing unit 113 that computes a resonance frequency corresponding to the magnitude of the external force F2 calculated by the calculator 111.

The controller 110 includes a drive controller (drive control unit) 115 that drives the vibrator 100 in such a manner that the vibrator 100 vibrates at the resonance frequency computed by the computing unit 113.

Thus, the controller 110 calculates the magnitude of the external force F2 applied to the insertion section 30 from the tube 200 on the basis of the states of the insertion section 30, computes the resonance frequency of the vibration relative to the magnitude of the external force F2, and controls the vibrator 100 in such a manner that the vibrator 100 vibrates at the resonance frequency. The controller 110 starts the control when an operation section (not shown) is operated, and constantly performs the control. The timing of the control may be at every predetermined period of time, and is not limited to a particular timing.

Figure 4A:
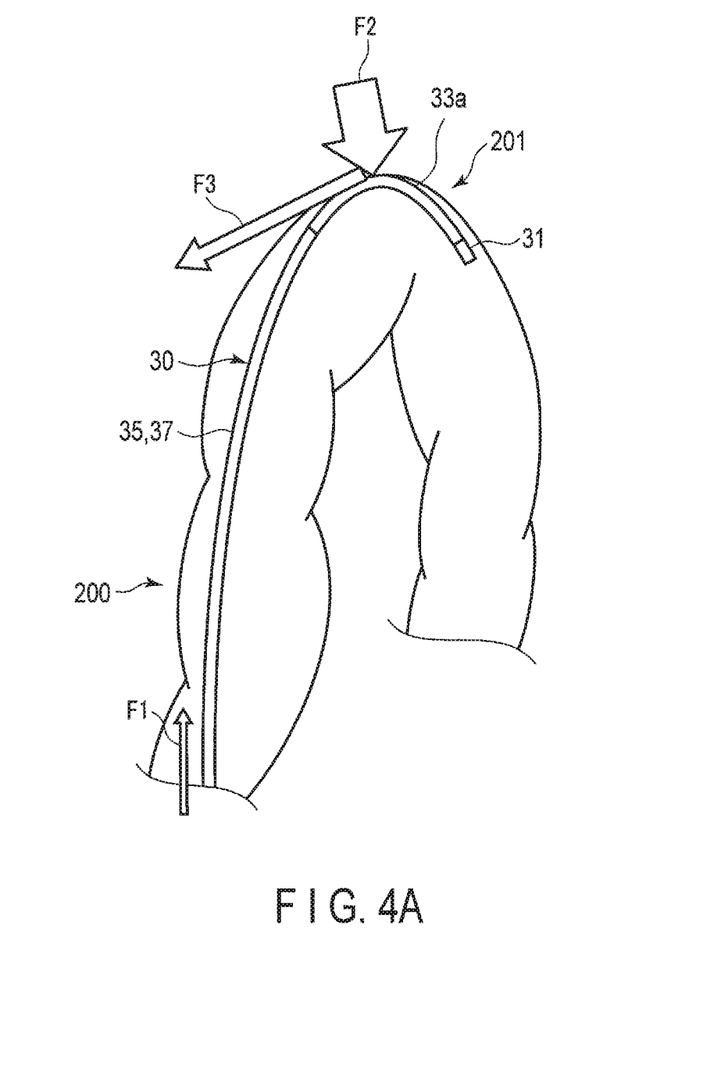
FIG. 4A illustrates a state in which an external force and a frictional force act on an insertion section when a distal end portion of the insertion section passes through a bent section.

When the proximal end portion of the insertion section 30 is gripped, the insertion section 30 is inserted into the tube 200, and the entire insertion section 30 is pressed. Let us assume that, as shown in FIG. 4A, the distal end portion of the insertion section 30 passes through a bent section 201 of the tube 200, such as the large intestine.

The active bendable portion 33a is bent by the bendable operation portion 41, causing the bending radius of the active bendable portion 33a to correspond to the bending radius of the bent section 201. At the same time, the entire insertion section 30 is pressed by the insertion force F1 and passes through the tube 200. In this state, the active bendable portion 33a contacts the bent section 201, and the active bendable portion 33a receives the external force F2 as a reaction force against the insertion force F1 of the insertion section 30 in the contact portion. In the tube 200, a resistive force is generated as a reaction force against the external force F2, and a frictional force F3 corresponding to the resistive force prevents the passage of the insertion section 30.

Figure 4B:
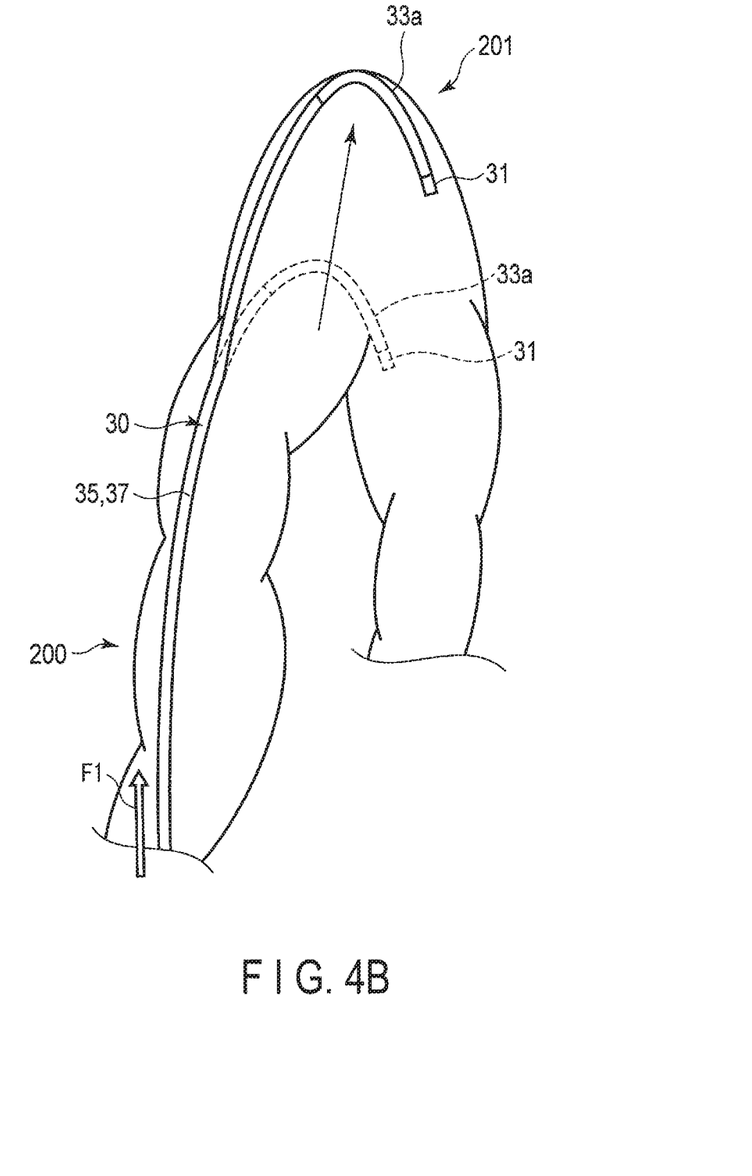
FIG. 4B is a diagram illustrating a state in which an active bendable portion pushes up a tube.

The states of the insertion section 30 inserted into the tube 200 changes according to, for example, the insertion force F1 or the external force F2, and the frictional force F3 changes according to the change in the states of the insertion section 30. If at least one of the detection unit 90, the vibrator 100, and the controller 110 were not provided, unlike the present embodiment, the states of the insertion section 30, namely, the optimum vibration corresponding to the changed frictional force F3 would not be constantly generated with ease due to a lack of at least one of them, and the ease of insertion of the insertion section 30 would not be reliably improved to the maximum extent. Accordingly, the active bendable portion 33a would not slide over an inner peripheral surface of the bent section 201 with the frictional force F3, and the distal end portion of the insertion section 30 would not advance along the bent section 201 with the frictional force F3, during passage of the insertion section 30 with the insertion force F1. Depending on the situation, the active bendable portion 33a may push up the bent section 201 with the insertion force F1, as shown in FIG. 4B, causing distress to the patient.

Figure 4C:
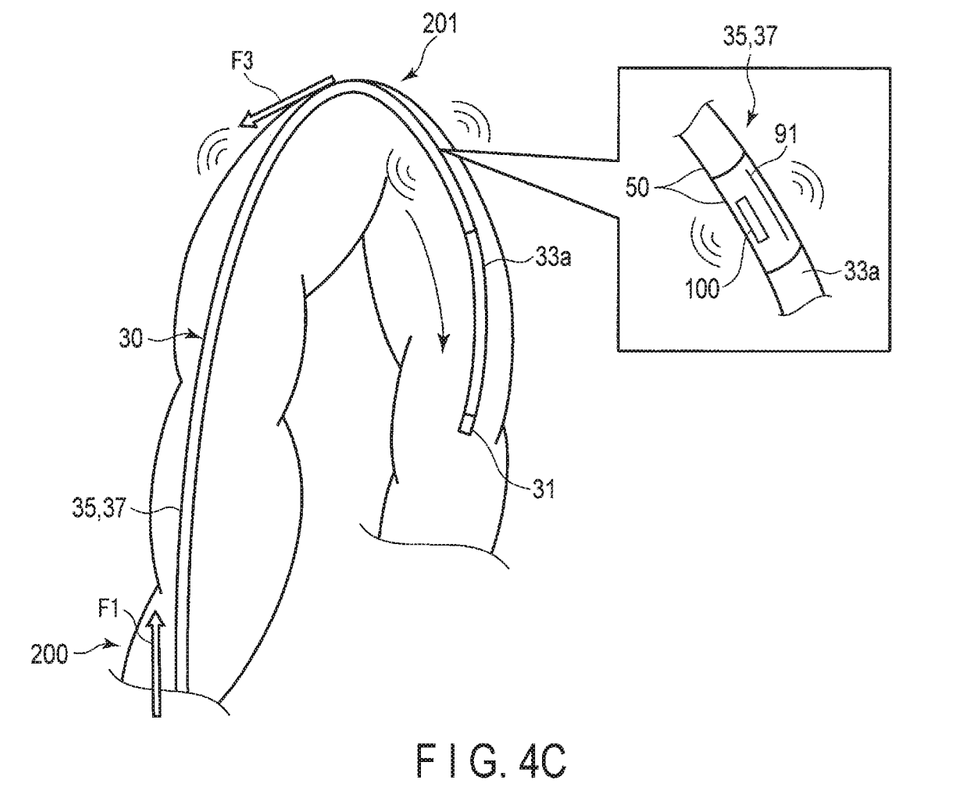
FIG. 4C is a diagram illustrating a state in which vibration of the vibrator reduces the frictional force, allowing the insertion section to be advanced with less insertion force, thereby improving the ease of insertion of the insertion section.

In the present embodiment, however, the detection unit 90 constantly detects the states of the insertion section 30, including the case where the active bendable portion 33a contacts the bent section 201. One of states of the insertion section 30 is one of the bending radius, the bending strain, and the pressure of the insertion section 30. The calculator 111 of the controller 110 calculates the magnitude of the external force F2 applied to the insertion section 30 from the tube 200 on the basis of the states of the insertion section 30. Next, the computing unit 113 of the controller 110 computes a resonance frequency corresponding to the magnitude of the external force F2 calculated by the calculator 111. The drive controller 115 of the controller 110 drives the vibrator 100 in such a manner that the vibrator 100 vibrates at the resonance frequency. As shown in FIG. 4C, the vibrator 100 vibrates at the resonance frequency in a state in which the insertion section 30 contacts the tube 200 including the bent section 201.

The frictional force F3 is reduced by the vibration, and the insertion section 30 advances with the less insertion force F1, thus improving the ease of insertion of the insertion section 30.

In the present embodiment, in particular, the detection unit 90 constantly detects the states of the insertion section 30, even when the frictional force F3 changes according to the states of the insertion section 30 inserted into the tube 200. The vibrator 100 vibrates at the resonance frequency corresponding to the states of the insertion section 30, namely, at the resonance frequency corresponding to the changed frictional force F3. Accordingly, the vibration enables a maximum reduction of the frictional force F3 corresponding to the states of the insertion section 30 inserted into the tube 200. It is thus possible in the present embodiment to reliably improve the ease of insertion of the insertion section 30 to the maximum extent upon occurrence of vibration.

In the present embodiment, the resonance frequency of the vibration corresponds to the states of the insertion section 30, namely, the frictional force F3, and is constantly calculated by the calculator 111. The optimum vibration corresponding to the changed frequency is constantly generated with ease.

In the present embodiment, the states of the insertion section 30 are constantly detected, and vibration occurs at the resonance frequency corresponding to the result of detection. It is thus possible in the present embodiment to constantly generate the optimum vibration corresponding to the changed friction with ease, and to reliably improve the ease of insertion of the insertion section 30 to the maximum extent.

In particular, it is possible to reduce the frictional force F3 by vibration, advance the insertion section 30 with the less insertion force F1, and to improve the ease of insertion of the insertion section 30. Since the frictional force F3 can be reduced by vibration at the resonance frequency, the insertion section 30 can be reliably advanced. It is thus possible to prevent the insertion section 30 from pushing up the bent section 201 with the insertion force F1, as shown in FIG. 4B, and causing distress to the patient. The resonance frequency of vibration is constantly controlled by the controller 110. That is, the resonance frequency of vibration is not manually adjusted. This eliminates the need for the operation to set a resonance frequency of the vibration corresponding to the changed frictional force F3 every time the frictional force F3 changes, thus eliminating the inconvenience of setting.

The vibrator 100 is arranged at the distal end portion of the flexible tube 35, which is the interposed section 37.

Accordingly, the vibration of the vibrator 100 reliably acts on the active bendable portion 33a, the frictional force F3 in the active bendable portion 33a can be reduced, and the active bendable portion 33a can be easily bent. Thus, the bending of the active bendable portion 33a results in improvement in the ease of insertion of the insertion section 30.

In the present embodiment, the calculator 111 constantly calculates the magnitude of the external force F2 applied to the insertion section 30 from the tube 200 on the basis of the states of the insertion section 30, which is a result of detection of the state detector 91. However, the present embodiment is not limited thereto.

The calculator 111 determines whether or not the bending radius of the insertion section 30, which is one of states of the insertion section 30, is less than a preset threshold value. If the calculator 111 determines that the bending radius is less than the threshold value, the calculator 111 may calculate the magnitude of the external force F2 applied to the insertion section 30.

Alternatively, the calculator 111 determines whether or not the bending strain of the insertion section 30, which is one of the states of the insertion section 30, is greater than a preset threshold value. When the calculator 111 determines that the bending strain is greater than the threshold value, the calculator 111 may calculate the magnitude of the external force F2 applied to the insertion section 30.

Alternatively, the calculator 111 determines whether or not a pressure that is a load applied to the insertion section 30, which is one of the states of the insertion section 30, is greater than a preset threshold value. If the calculator 111 determines that the pressure is greater than the threshold value, the calculator 111 may calculate the magnitude of the external force F2 applied to the insertion section 30.

In the present embodiment, the computing unit 113 constantly computes the resonance frequency corresponding to the magnitude of the external force F2 calculated by the calculator 111, but the computing is not limited thereto.

The computing unit 113 determines whether or not the external force F2 is greater than a preset threshold value. If the computing unit 113 determines that the external force F2 is greater than the threshold value, the computing unit 113 may compute the resonance frequency corresponding to the magnitude of the external force F2.

Second Embodiment

Figure 5:
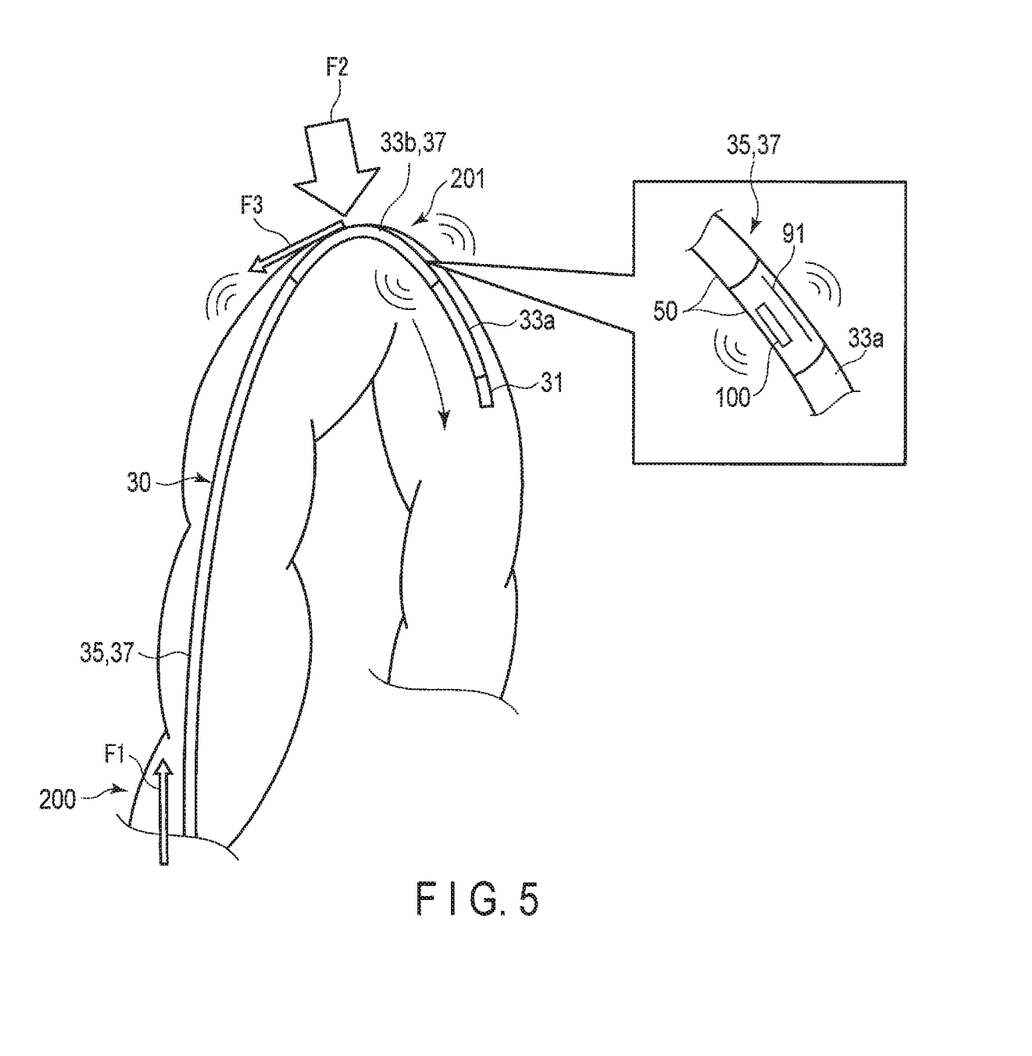
FIG. 5 is a diagram illustrating a state in which vibration of a vibrator during passage of a distal end portion of an insertion section through a bent section reduces a frictional force, allowing the insertion section to be advanced with less insertion force, thereby improving the ease of insertion of the insertion section, according to a second embodiment of the present invention.

Hereinafter, only the structures different from those of the first embodiment will be described with reference to FIG. 5. The present embodiment is different from the first embodiment in the structure of the insertion section 30.

The insertion section 30 comprises, in the order from a distal end portion of the insertion section 30 to a proximal end portion of the insertion section 30, a distal rigid portion 31, an active bendable portion 33a, a passive bendable portion 33b, and a flexible tube 35. A proximal end portion of the active bendable portion 33a is coupled to a distal end portion of the passive bendable portion 33b, and a proximal end portion of the passive bendable portion 33b is coupled to a distal end portion of the flexible tube 35.

The flexible tube 35 has a length greater than that of the passive bendable portion 33b. The distal end portion of the flexible tube 35 may include the passive bendable portion 33b.

Upon receipt of an external force F2, the passive bendable portion 33b is passively bent by the external force F2. The maximum bending radius of the passive bendable portion 33b is greater than the maximum bending radius of the active bendable portion 33a, and is smaller than the maximum bending radius of the flexible tube 35. Accordingly, the curvature of the insertion section 30 increases stepwise from the distal end portion of the insertion section 30 toward the proximal end portion of the insertion section 30.

An interposed section 37 functions as the passive bendable portion 33b and the flexible tube 35.

A vibrator 100 is arranged at the distal end portion of the passive bendable portion 33b, which is the interposed section 37. The vibrator 100 may be arranged in the flexible tube 35.

In the present embodiment, the vibrator 100 vibrates at the resonance frequency in a state in which the passive bendable portion 33b is in contact with the tube 200 including the bent section 201. This reduces a frictional force F3 between the passive bendable portion 33b and the tube 200. Since the curvature of the insertion section 30 increases stepwise, the insertion section 30 smoothly bends, allowing the insertion section 30 to smoothly pass through the bent section 201 without locally applying a resistive force to the tube 200.

Third Embodiment

Figure 6:
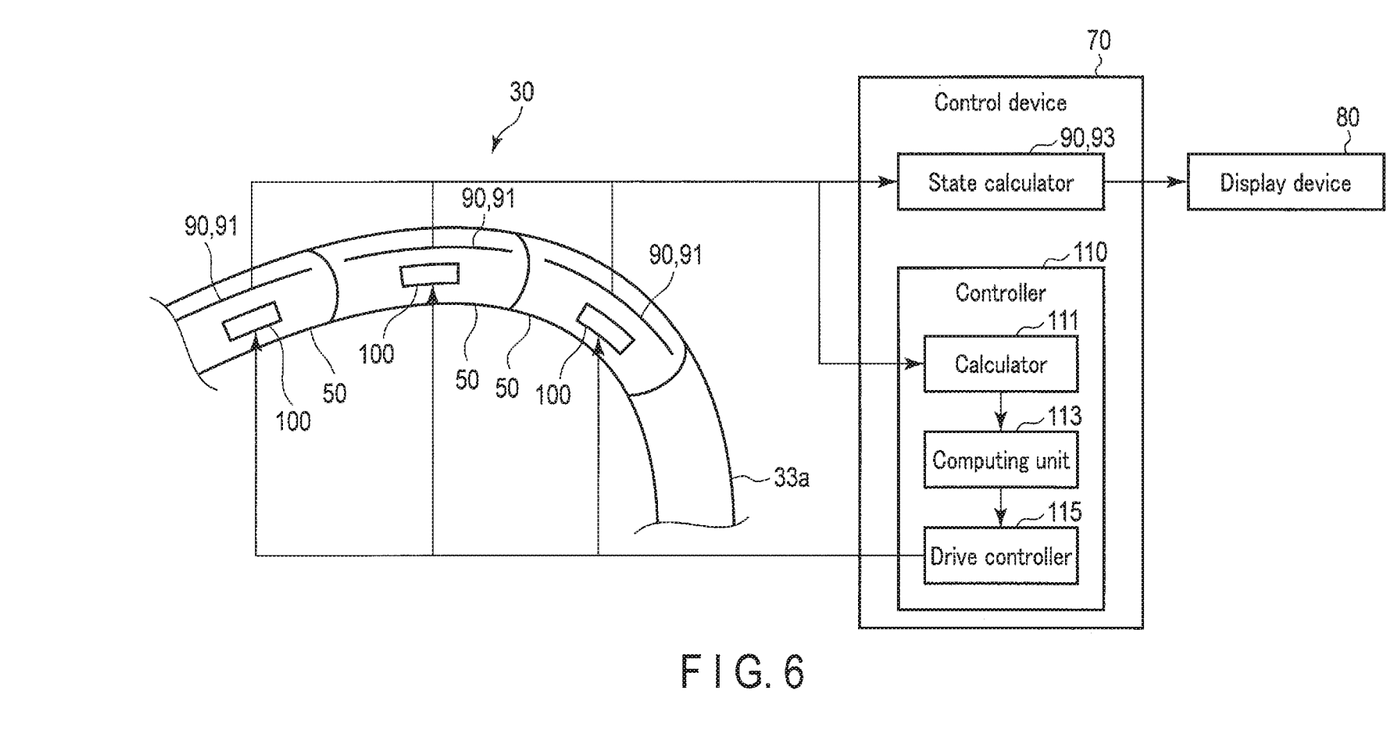
FIG. 6 is a diagram illustrating a relationship between segments, a detection unit, a controller, and a vibrator according to a third embodiment of the present invention.

Hereinafter, only the structures different from those of the first embodiment will be described with reference to FIG. 6. In the present embodiment, a plurality of vibrators 100 are arranged in such a manner that the vibrators 100 are apart from each other along an axial direction of an insertion section 30. For example, one vibrator 100 and one state detector 91 are arranged in each segment 50 as a unit.

A controller 110 is shared by each unit. The controller 110 may be arranged in each unit. The controller 110 controls the resonance frequency of vibration generated by the vibrator 100 for each unit.

In the present embodiment, the vibrators 100 are arranged throughout the insertion section 30. Since a frictional force F3 is reduced in the entire insertion section 30, the insertion section 30 can be advanced with a less insertion force F1, thus further improving the ease of insertion of the insertion section 30.

The present invention is not limited to the above-described embodiments and can be embodied in practice by modifying the structural elements without departing from the gist of the invention. In addition, various inventions can be made by properly combining the structural elements disclosed in connection with the above embodiments.

What is claimed is:

1. A flexible tube insertion apparatus comprising:
    an insertion section configured to be inserted into a tubular body;
    one or more detection sensors each configured to detect one or more states of the insertion section;
    one or more vibration actuators that are arranged in the insertion section, the one or more vibration actuators each being configured to generate vibration to vibrate the insertion section by the generated vibration; and
    a controller configured to:
        calculate a magnitude of an external force applied to the insertion section from the tubular body based on the one or more states of the insertion section detected by the one or more detection sensors,
        compute a resonance frequency of the vibration relative to the magnitude of the external force, and
        control the one or more vibration actuators to vibrate at the resonance frequency.

2. The flexible tube insertion apparatus according to claim 1, wherein the one or more states of the insertion section comprises one or more of a bending radius of the insertion section, a bending strain of the insertion section, and a pressure applied to the insertion section, which are included in the states of the insertion section.

3. The flexible tube insertion apparatus according to claim 2, wherein
    when the one or more detection sensors detect the bending radius of the insertion section,
    the controller calculates the magnitude of the external force upon determining that the bending radius is smaller than a preset threshold value.

4. The flexible tube insertion apparatus according to claim 2, wherein
    when the one or more detection sensors detect the pressure applied to the insertion section,
    the controller calculates the magnitude of the external force upon determining that the pressure is greater than a preset threshold value.

5. The flexible tube insertion apparatus according to claim 2, wherein
    when the one or more detection sensors detect the bending strain of the insertion section,
    the controller calculates the magnitude of the external force upon determining that the bending strain is greater than a preset threshold value.

6. The flexible tube insertion apparatus according to claim 1, wherein the controller computes the resonance frequency corresponding to the magnitude of the external force upon determining that the external force is greater than a preset threshold value.

7. The flexible tube insertion apparatus according to claim 1, herein
    the insertion section includes an active bendable portion that actively bends in response to an operation of an operation section coupled to the insertion section, and
    the one or more vibration actuators are arranged adjacent to the active bendable portion.

8. The flexible tube insertion apparatus according to claim 7, wherein
    the insertion section further comprises an interposed section interposed between the active bendable portion and the operation section,
    the interposed section includes a distal end portion coupled to a proximal end portion of the active bendable portion, and
    the one or more vibration actuators are arranged at the distal end portion of the interposed section.

9. The flexible tube insertion apparatus according to claim 8, wherein the interposed section is a passive bendable portion.

10. The flexible tube insertion apparatus according to claim 1, wherein the one or more vibration actuators comprise two or more vibration actuators, two of the two or more vibration actuators being arranged apart from each other along an axial direction of the insertion section.

11. The flexible tube insertion apparatus according to claim 1, wherein
    the insertion section is partitioned into a plurality of segments spaced apart from one another along an axial direction, and
    each of the plurality of segments includes one of the one or more vibration actuators and one of the one or more detection sensors.

12. The flexible tube insertion apparatus according to claim 1, wherein each of the one or more vibration actuators comprise a motor and a weight attached to the motor in an eccentric state.

13. The flexible tube insertion apparatus according to claim 1, wherein each of the one or more vibration actuators comprise a voice coil motor.

14. The flexible tube insertion apparatus according to claim 1, wherein each of the one or more vibration actuators comprise a vibrating body having a piezoelectric element.

* * * * *